United States Patent
Tovena-Pecault

(10) Patent No.: US 8,592,222 B2
(45) Date of Patent: Nov. 26, 2013

(54) METHOD FOR ANALYSING MOLECULAR POLLUTION OF A FLUID, APPLICATION DEVICE AND APPLICATION TO THE ANALYSIS OF POLLUTION IN A NATURAL MEDIUM AND IN A CONTROLLED ENVIRONMENT

(75) Inventor: Isabelle Tovena-Pecault, Leognan (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 191 days.

(21) Appl. No.: 13/122,671

(22) PCT Filed: Oct. 9, 2009

(86) PCT No.: PCT/EP2009/063142
§ 371 (c)(1),
(2), (4) Date: May 13, 2011

(87) PCT Pub. No.: WO2010/040817
PCT Pub. Date: Apr. 15, 2010

(65) Prior Publication Data
US 2011/0217789 A1    Sep. 8, 2011

(30) Foreign Application Priority Data
Oct. 10, 2008    (FR) ...................................... 08 56877

(51) Int. Cl.
*G01N 1/22*    (2006.01)
(52) U.S. Cl.
USPC ............... 436/181; 436/38; 436/145; 438/14; 438/16; 438/115; 356/36; 422/89

(58) Field of Classification Search
None
See application file for complete search history.

(56) References Cited

U.S. PATENT DOCUMENTS

| | | |
|---|---|---|
| 5,832,411 A | 11/1998 | Schatzmann et al. |
| 2005/0053515 A1 | 3/2005 | Yates et al. |
| 2006/0258017 A1 | 11/2006 | Gullett et al. |
| 2008/0009099 A1 | 1/2008 | Kishkovich et al. |

FOREIGN PATENT DOCUMENTS

| | | |
|---|---|---|
| WO | WO 2004/097399 A2 | 11/2004 |
| WO | WO 2004/097399 A3 | 11/2004 |
| WO | WO 2006/022491 A1 | 3/2006 |
| WO | WO 2008/074843 A1 | 6/2008 |

OTHER PUBLICATIONS

Search Report issued May 20, 2009 in French Patent Application No. FA 713311 (with English Translation of Category of Cited Documents).
NF EN ISO 14644-8, "Cleanrooms and Associated Controlled Environments—Part 8: Classification of Airborne Molecular Contamination (ISO 14644-8:2006)", Nov. 2006, 27 pages (English version).

*Primary Examiner* — Robert Xu
(74) *Attorney, Agent, or Firm* — Oblon, Spivak, McClelland, Maier & Neustadt, L.L.P.

(57) ABSTRACT

A method for analyzing molecular pollutants of a fluid. From a calibrated flow of fluid, a combination of a measurement of a total amount of molecular pollutants and a determination of chemical compositions and relative amounts of the molecular pollutants by adsorption on materials is carried out. The determination of the chemical compositions and relative amounts advantageously occur after a threshold value for the total measured amount is exceeded.

6 Claims, 2 Drawing Sheets

METHOD FOR ANALYSING MOLECULAR POLLUTION OF A FLUID, APPLICATION DEVICE AND APPLICATION TO THE ANALYSIS OF POLLUTION IN A NATURAL MEDIUM AND IN A CONTROLLED ENVIRONMENT

TECHNICAL FIELD

The invention relates to the field of non-particulate pollution or in other words, molecular pollution of a fluid.

The invention relates to the analysis of this type of pollution which occurs in a given environment and to the study of its mode of deposition on different materials or types of biological tissues.

The fluid for which analysis of molecular pollution is sought, may within the scope of the invention be both a liquid and a gas.

The applications targeted by the invention are numerous. It may concern the analysis of molecular pollution present in natural media, clean rooms or areas with a related controlled environment, i.e. knowledge of materials (or nanomaterials), notably from the field of ultra-cleanliness.

It may also concern chemical environmental pollution. It may finally concern other fields: radiochemistry, combating terrorism, chemical safety, health-care establishments, research in the pharmaceutical field.

PRIOR ART

Molecular contamination is designated in the ISO 14644-8 standard by a (non-particulate) molecular species which may have an undesirable effect on the product, the method or the equipment.

Molecular contamination may be of the airborne type and classified as such in the recent ISO 14644-8 standard.

The contamination may also be of the surface type. Depending on its molecular mass and on the environmental conditions, the molecule will more or less tend to be deposited on such and such a surface. The sorption and/or reaction capability of these molecules, once they are deposited on surfaces, essentially depends on the chemical functional groups of the molecule. It also depends on geometrical characteristics (roughness, irregularities, particle cleanliness . . . ) and on chemical characteristics of the surfaces and finally on environmental conditions (notably temperature, pressure, hygrometry and particle contamination).

To this day, two types of measurement exist and are each limited to a type of molecular contamination. As regards airborne molecular contaminants, they may be sampled from a certain volume of gas defined beforehand and then set on adsorbent materials, such as Tenax®. When adsorption has been actually achieved, the actual analysis of these different molecular contaminants then consists of carrying out desorption, in particular by thermal desorption for example in the gaseous phase, and of then carrying out gas phase chromatography coupled with mass spectrometry (Gas Chromatography-Mass Spectrometry or GC/MS).

The total amount of molecular contaminants of the surface type may be continuously tracked by acoustic or gravimetric sensors. These may be Quartz Crystal Microscales (QCM) which has the advantage of higher sensitivity, of the order of a few angstroms per cm².

The operating principal of quartz microscales is the following: the quartz vibration frequency is evaluated as a quantity. Now, the latter is related to the mass of the material through the following equation:

$$\Delta F/F_0 = K\, m_{ads}$$

wherein:

$F_0$ is the rated frequency of the quartz (Hz);

$\Delta F$ is the frequency change of the quartz due to gas adsorption (Hz);

K is the characteristic constant of the quartz ($kg^{-1}$);

$m_{ads}$: the adsorbed gas mass (kg).

Conventionally, the rated frequency of quartz scales is of the order of 1 MHz, the mass sensitivity is of the order of a few angstroms per $cm^2$.

These may also be surface acoustic wave (SAW) detectors. The operating principle of these SAW sensors is the variation of the characteristics of these waves (amplitude and velocity) resulting from chemical and then mechanical modifications of its propagation medium.

Thus, in a controlled environment, in which a manufacturing process occurs in line, the obtained measurements are very global (amounts of molecules deposited on a surface and therefore initially present in the gas to be analyzed) but, they do not by any means give information on the chemistry of these molecules or on their mode of deposition on a surface other than that of the quartz.

In order to obtain the qualitative and quantitative analysis of such molecules in the gas, an adsorption phase is required on an adsorbent material with a very large specific surface area of the Tenax® type. Now, as mentioned above, in order to be sure that adsorption is achieved, up to now, a large gas volume is defined and therefore an <<exposure>> of the adsorbent to the gas to be analyzed, which is sufficiently long without knowing the amount of molecular contaminants with a given composition actually present. The major risk of this technique is therefore to obtain at the end of the predefined exposure time, adsorbents either completely saturated by certain species of contaminants, in particular in manufacturing methods which emit highly polluting phases, or, on the contrary, within detection limits in ultra-clean environments. The GC/MS analysis which follows may thus prove to be completely unnecessary since it may not take into account the amount of molecules in addition to those which have saturated the adsorbent(s). In other words, the samples of adsorbents cannot really be analyzed or at the very least they may induce a distorted analysis. Further, each analysis is expensive. Further, the <<excess>> of non-molecular pollutants which is not analyzed because of the saturation of the adsorbent (also called <<piercing>> of the material) may have damageable consequences on the surfaces of sensitive materials in the environment, such as a medium in a clean room.

The object of the invention is therefore to propose a solution which allows a reliable quantitative and qualitative analysis of the molecular contaminants present in an environment.

A particular object is to accurately know which chemical compositions and which amount of a given chemical composition of molecular contaminants may be deposited on sensitive surfaces of the environment.

DISCUSSION OF THE INVENTION

To do this, the object of the invention is a method for analyzing molecular pollution on a fluid according to which the following steps are carried out:

a) producing a calibrated flow of fluid, b) filtering the fluid with a calibrated flow in order to obtain the particulate and/or nanoparticulate pollutants, c) measuring in real time the total amount of molecular pollutants present in the fluid with a calibrated flow and upstream from the filtration, d) determining chemical compositions and the relative amount of molecular pollutants adsorbed in at least one sample made in adsorbent material(s) placed on the circuit of the fluid with a calibrated flow downstream from the measurement of the total amount, the determination occurring simultaneously and/or at predetermined time intervals relatively to an instant when a threshold value of the total amount of molecular pollutants present in the fluid with a calibrated flow rate and measured in real time is exceeded.

Thus, according to the invention, the analyses by desorption on the sample(s) of adsorbent material(s) are only carried out after having measured the sufficient total amount of molecular pollutants.

By means of the invention, it is possible to accurately know the amount of such and such molecule deposited on the surface of such and such material of an environment with known temperature and pressure conditions. In particular, it is possible to determine the pollutant molecules especially deposited on the surfaces of materials sensitive to an industrial environment under controlled temperature and pressure conditions.

The solution according to the invention meets a need emerging from the control of the level of contamination or atmospheric molecular pollution or pollution deposited on the surface of sensitive materials of an environment.

The fluid for which analysis of the molecular pollution is sought, may be a gas or a fluid. In the case of the liquid, the latter will be selected in order to somewhat form a vector of molecular pollutants present in an environment, typically on contaminated surfaces.

According to one feature, the sample(s) made in adsorbent material(s) is (are) suitable for adsorbing organic molecules.

It is possible to provide several samples of adsorbent material(s) with a different adsorption capacity placed on the circuit of the fluid with a calibrated flow downstream from the measurement of the total amount.

Advantageously, the determination of the chemical compositions of the pollutants is begun with the sample(s) of adsorbent material(s) having higher adsorption capacity. This may advantageously be Tenax®. It has the advantage of being an adsorbent polymeric phase highly used for extracting volatile organic compounds in air.

The other adsorbent materials may be formed by materials representative of sensitive materials of clean rooms. They may also consist in aluminium, stainless steel 304 or 316L, or in an optionally treated silica-based glass. In the field of biological analysis, the studied sensitive materials may be representative of biological tissues or of living cells.

In order to study the effect of the temperature and hygrometry conditions on adsorption by a sensitive material of the environment, the temperature of the fluid with a calibrated flow is advantageously controlled and when the fluid is a gas, the hygrometry of the gas with a calibrated flow is also controlled.

The determination of chemical compositions and relative amounts of the molecular pollutants adsorbed on the sample(s) made in adsorbent material may be carried out in situ, by coupling with means for extracting the adsorbents from the fluid (liquid or gas) and with chromatographic analysis means themselves coupled with mass spectrometry.

They may also according to an alternative be carried out ex situ by removing the sample(s) from the circuit of the fluid with calibrated flow and treatment in a desorption unit.

When the fluid is a liquid, an analysis according to a LCMS (Liquid Chromatography Mass Spectrometry) technique is advantageously carried out.

The invention also relates to a device for analyzing molecular pollution of a fluid present in an environment comprising:
  means for calibrating a fluid flow,
  means for particle filtration of the fluid with calibrated flow in order to retain the particulate pollutants,
  means for measuring in real time the total amount of molecular pollutants present in the fluid with calibrated flow, said measurement means being laid out on the circuit of the fluid with a calibrated flow downstream from the filtration means,
  alarm means for when the total amount of non-particulate pollutants present in the fluid with a calibrated flow is in excess,
  at least one sample made in an adsorbent material placed on the circuit of the fluid with calibrated flow downstream from the measurement of the total amount,
  means for determining the chemical compositions and their relative amount in the sample(s) made in adsorbent material(s).

The filtration means may be a filter with meshes having a size of typically less than 0.2 µm.

The means for calibrating a flow of the fluid may comprise a pump placed downstream from the sample(s) made in adsorbent material(s). Optionally, the calibration means comprise a pressure gauge and/or a flowmeter.

The means for measuring in real time the total amount of non-particulate pollutants may comprise at least one sensor of the acoustic or gravimetric type. This or these sensors is(are) preferably used for their accuracy today ranging up to one Å/cm². It is also possible to use optical analysis means (ellipsometry, Fourier Transform InfraRed Spectrometry (FTIR) . . . ).

For a liquid or a gas to be analyzed, quartz micro-scales may be used with a sensitivity adapted to liquid or gas. Typically, the sensitivity threshold of quartz microscales for analyzing molecules in a liquid will be of the order of a few Å/cm², and for analyzing a gas also of the order of a few Å/cm².

The means for determining the chemical compositions and their relative amount in the sample(s) made in adsorbent material(s) advantageously comprise a thermo-desorption unit and an assembly applying liquid or gas phase chromatography coupled with mass spectrometry (Gas Chromatography-Mass Spectrometry or GC/MS).

The device may comprise:
  a conveying assembly of the carousel type laid out so as to be rotatably mounted in the fluid circuit upstream from the means for measuring in real time the total amount of molecular pollutants, the carousel comprising a plurality of supports adapted for each supporting an adsorbent material sample,
  a sealed system of the airlock type laid out adjacent to the fluid circuit, the layout of the airlock giving the possibility of individually removing a sample of adsorbent material(s) from its support in a given position of the carousel while continuing real-time measurement of the total amount of molecular pollutants present in the fluid with calibrated flow and adsorption of the molecular pollutants by the other samples of adsorbent material(s) maintained on their respective support.

The airlock may comprise a desorption unit such as an oven for thermo-desorption and is connected to a GC/MS assembly in order to carry out in real time and continuously the determination of the chemical compositions and of their relative amount on the sample made in adsorbent material(s). The airlock may also comprise a reactor for liquid extraction and then analysis by LCMS.

Advantageously, provision may be made for making all the components present in the circuit of fluid with a calibrated flow (particle filter, walls of the circuit per se, means for measuring the total amount in real time, carousel . . . ) in chemically inert or neutral materials. A definition of a neutral material is given in the patent application of the applicants published under number WO 2008/074843: this may thus be PTFE on stainless steel or silica inactivated by dimethyldichlorosilane.

The invention finally relates to the application of the method or of the device defined above for analyzing the pollution of a natural medium or the cleanliness of chemical synthesis, part manufacturing or experimental lines, such as clean rooms.

Advantageously, the invention applies to certain industries (space industry, micromechanics, optics, nanotechnologies but also the pharmaceutical and food processing industry, hospitals . . . ), in which controlling the level of chemical or biochemical contamination on the process/product/patient is a vital requirement for biological cells or tissues, living organisms (bacteria . . . ). Thus, the invention gives the possibility of producing an alert on the growth in situ of chemically critical molecular films as regards such and such functional surface of an environment in which ultra-cleanliness conditions are sought to be achieved (space industry, microelectronics, optics, power lasers, pharmacy, medical research, health-care establishments . . . ).

BRIEF DESCRIPTION OF THE DRAWINGS

Other advantages and features will become better apparent upon reading the detailed description of the invention, as an illustration, made with reference to FIGS. 1 and 2 which illustrate.

DETAILED DISCUSSION OF PARTICULAR EMBODIMENTS

Figure 1:
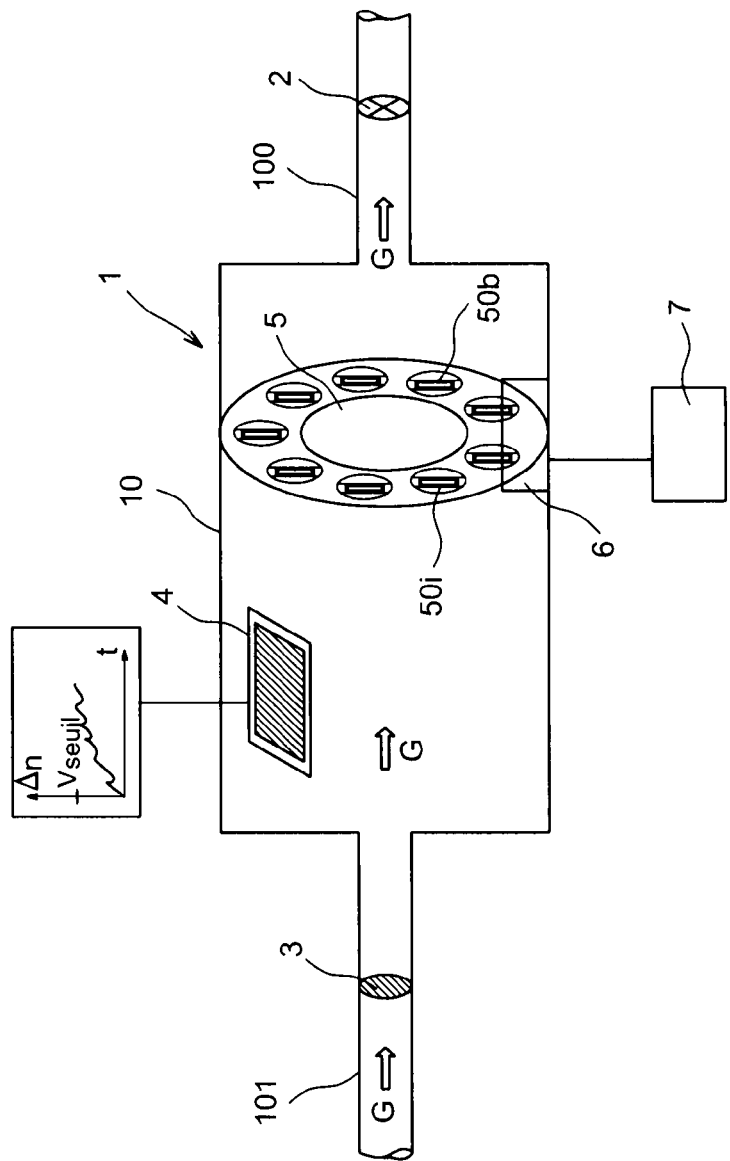
FIG. 1: a schematic view of a device for analyzing molecular pollution of a fluid according to an embodiment of the invention.

A device 1 for analyzing molecular pollution present in an environment is schematically illustrated in FIG. 1.

This device 1 comprises a circuit 10 for which aeraulics is under control: it comprises a single channel 100 connected to a suction pump 2 with a calibrated flow rate.

Thus, the operating pump 2 sucks up a calibrated gas flow G from the environment for which analysis of molecular pollution is sought.

In proximity to the suction inlet 101, a particle filter 3 is implanted in the circuit in order to filter the molecules and to retain the particles present in the gas for which analysis of the polluting molecules is sought.

Downstream from the filter 3, is implanted a sensor of the quartz microscales type 4 with which it is possible to determine the total amount $\Delta m$ of polluting molecules versus time t.

Figure 2:
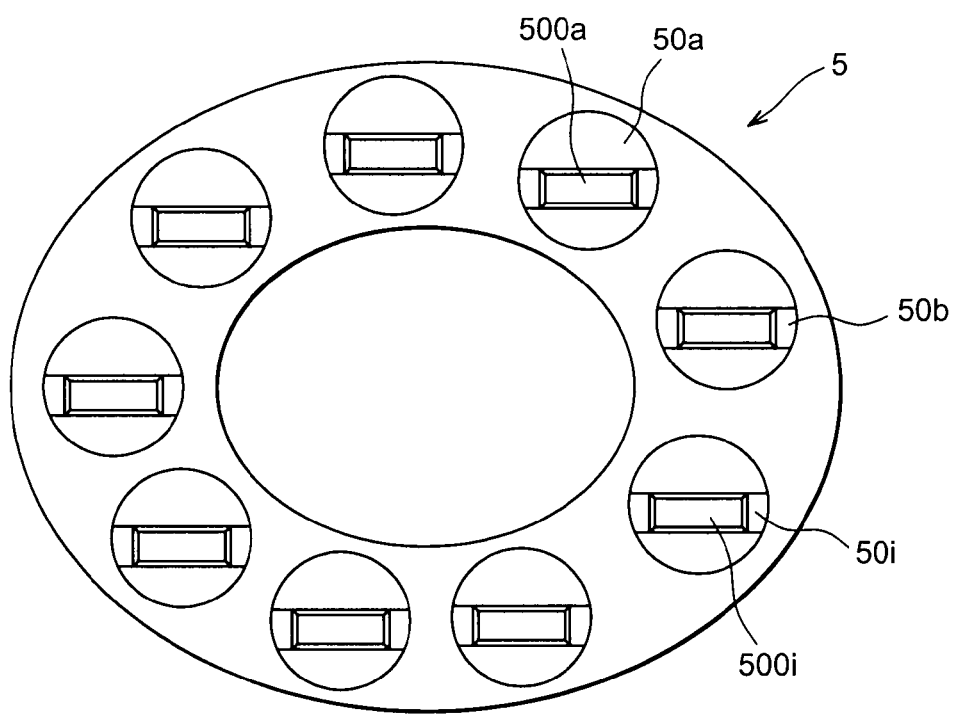
FIG. 2: a schematic view of a portion of the device according to FIG. 1 and illustrating the adsorption of molecular pollutants according to the invention.

Downstream from the quartz microscales 4, a conveying assembly of the carousel type 5 is laid out so as to be rotatably mounted in the fluid circuit. This carousel 5 comprises a plurality of supports $50a, 50b, \ldots 50i$ adapted so as to each support an adsorbent material sample $500a, 500b \ldots 500i$ (FIG. 2). A sample $500a$ of Tenax® is preferably used as a sample of greater adsorption capacity. This material has the advantage of being an adsorbent polymeric phase allowing extraction of volatile organic compounds from air.

A sealed airlock 6 is laid out adjacent to the fluid circuit 10. The layout of the airlock 6 gives the possibility of individually removing an adsorbent material sample 500 from its support in a given position of the carousel. As illustrated in FIG. 1, the sample which is found in the airlock 6 is a sample of Tenax® $500a$.

The airlock 6 further comprises a desorption oven coupled with a GC/MS unit 7.

The operation of the device 1 will now be described.

The device 1 is first placed in the environment for which molecular pollution determination is sought.

A calibrated gas flow G is established by triggering the pump 2.

The particulate pollutants present in the gas G are then filtered by the filter 3 laid out in the upstream portion of the circuit 10.

The quartz microscales 4 then continuously measure the total amount of molecular pollutants present in the gas G at a calibrated flow and free of particular pollutants.

The rotation of the carousel 5 is permanent as long as the threshold value V is not exceeded and this, in order to be able to have a homogeneous medium.

When the total amount of molecular pollutants measured by the sensor 4 has exceeded a threshold value V, the carousel 5 is temporarily stopped so that a sample $500a$ initially swept by the calibrated gas flow G is isolated in the airlock 6 (FIG. 1). The extraction of the molecular pollutants may then begin.

The stopping of the carousel 5 may be carried out in quasi real time relatively to this instant.

With the operating desorption oven, it is then possible to detach the molecules adsorbed by the material simple $500a$.

The molecules desorbed by the oven are then analyzed in their chemical composition and their relative amounts by the GC/MS unit 7.

Regardless of the sample $500a, \ldots 500i$ which undergoes analysis, the real-time measurement of the total amount of molecular pollutants present in the fluid with calibrated flow and the adsorption of the molecular pollutants by the adsorbent material samples maintained on their respective support are continued. Analysis of the chemical composition and of the amounts relating to the molecular pollutants present in the other samples is then triggered when another threshold value is reached.

The whole of the walls of the gas G circuit 10 of the carousel 5 and of the airlock 6 are advantageously covered with Teflon® coating.

In order to study the influence of temperature and hygrometric conditions on the effect of adsorption of molecular pollutants, the device 1 may be provided with means for controlling, i.e. raising or lowering, the temperature, the hygrometry and the gas G pressure.

It is also possible to contemplate extraction via a liquid route (liquid chromatography).

The invention claimed is:

1. A device for analyzing molecular pollution of a fluid present in an environment, comprising:
   a calibration device for calibrating flow of the fluid;
   a filtration device for particle filtration of the fluid with calibrated flow to retain particulate pollutants;
   a measurement device for measuring in real time a total amount of the molecular pollutants present in the fluid with calibrated flow, the measurement device being laid out on a circuit of the fluid with calibrated flow downstream from the filtration device;
an alarm device for producing an alarm when the total amount of the molecular pollutants present in the fluid with calibrated flow is in excess;
at least one sample made in adsorbent material(s) placed on the circuit of the fluid with calibrated flow downstream from the measurement of the total amount;
a determination device for determining chemical compositions of the molecular pollutants and a relative amount thereof in the at least one sample made in adsorbent material(s), the determining being conducted simultaneously and/or at predetermined time intervals relatively to an instant when a threshold value of the total amount of molecular pollutants present in the fluid with calibrated flow and measured in real time is exceeded.

2. The device according to claim 1, wherein the calibration device for calibrating a flow of the fluid comprises a pump placed downstream from the at least one sample made in adsorbent material(s), or a pump and a pressure gauge and/or a flow meter.

3. The device according to claim 1, wherein the measurement device for measuring in real time the total amount of molecular pollutants comprises at least one sensor of acoustic or gravimetric type.

4. The device according to claim 1, wherein the determination device for determining the chemical compositions and the relative amount thereof in the at least one sample made in adsorbent material(s) comprises a thermo-desorption unit and an assembly applying liquid or gas phase chromatography coupled with mass spectrometry (liquid (LCMS), gas (GC/MS) chromatography-mass spectrometry).

5. The device according to claim 1, further comprising:
a conveying assembly of carousel type laid out so as to be rotatably mounted in the fluid circuit downstream from the measurement device for measuring in real time the total amount of molecular pollutants, the carousel comprising a plurality of supports adapted for each supporting a sample of adsorbent material(s); and
a sealed system of airlock type laid out adjacent to the fluid circuit, the layout of the airlock allowing a sample of adsorbent material(s) to be individually removed from its support in a given position of the carousel while continuing the real time measurement of the total amount of the molecular pollutants present in the fluid with calibrated flow and the adsorption of the molecular pollutants by the other samples of adsorbent material(s) maintained on their respective support.

6. The device according to claim 5, wherein the airlock comprises a desorption unit or an oven for thermo-desorption connected to a mass spectrometry GC/MS assembly to carry out in real time and continuously the determination of the chemical compositions and of their relative amount on the at least one sample made in adsorbent material(s).

* * * * *